(12) United States Patent
Ichikawa

(10) Patent No.: US 10,463,385 B2
(45) Date of Patent: Nov. 5, 2019

(54) SURGICAL INSTRUMENT

(71) Applicant: CHUKYO MEDICAL CO., INC., Atsuta-ku, Nagoya-shi, Aichi (JP)

(72) Inventor: Kazuo Ichikawa, Nagoya (JP)

(73) Assignee: CHUKYO MEDICAL CO., INC., Atsuta-Ku, Nagoya-Shi (JP)

( * ) Notice: Subject to any disclaimer, the term of this patent is extended or adjusted under 35 U.S.C. 154(b) by 238 days.

(21) Appl. No.: 15/654,276

(22) Filed: Jul. 19, 2017

(65) Prior Publication Data

US 2017/0311970 A1  Nov. 2, 2017

Related U.S. Application Data

(62) Division of application No. 14/238,117, filed as application No. PCT/JP2012/070599 on Aug. 13, 2012, now abandoned.

(30) Foreign Application Priority Data

Sep. 6, 2011 (JP) ................................ 2011-193780

(51) Int. Cl.
  *A61B 17/3203* (2006.01)
  *A61F 9/007* (2006.01)
  *A61B 17/3205* (2006.01)
  *A61B 17/00* (2006.01)
  *A61B 90/00* (2016.01)

(52) U.S. Cl.
  CPC ...... *A61B 17/3203* (2013.01); *A61B 17/3205* (2013.01); *A61F 9/00763* (2013.01); *A61F 9/00781* (2013.01); *A61B 2017/00544* (2013.01); *A61B 2090/08021* (2016.02)

(58) Field of Classification Search
  CPC ................ A61F 9/0133; A61F 9/00763; A61F 9/00781; A61B 17/3205; A61B 17/32053; A61B 17/320758; A61B 2090/08021
  See application file for complete search history.

(56) References Cited

U.S. PATENT DOCUMENTS

| | | | | |
|---|---|---|---|---|
| 5,106,364 A | * | 4/1992 | Hayafuji | A61B 17/32002 30/208 |
| 2006/0241580 A1 | | 10/2006 | Mittelstein | A61B 18/1482 606/41 |
| 2009/0287233 A1 | | 11/2009 | Huculak | A61F 9/00781 606/167 |

FOREIGN PATENT DOCUMENTS

| | | |
|---|---|---|
| JP | 2003-529402 A | 10/2003 |
| JP | 2005-185427 A | 7/2005 |
| JP | 2007-524472 A | 8/2007 |

(Continued)

*Primary Examiner* — Anh T Dang
(74) *Attorney, Agent, or Firm* — R. Neil Sudol; Henry D. Coleman

(57) ABSTRACT

A surgical instrument (1) is provided with a rigid probe (2), and cuts off the trabecular meshwork by inserting this probe (2) into the canal of Schlemm. An inner tube portion having a cutter is equipped inside the probe, and the trabecular meshwork sucked in from a hole portion (22) is cut off by the cutter due to the movement of the inner tube portion. A protection portion (21) is formed on the tip the probe (2) and protects the outer wall of the canal of Schlemm when cutting the trabecular meshwork. According to the invention, an ophthalmic surgical instrument for glaucoma patients is provided, the surgical instrument having excellent operability and preventing cutting of parts that should not be cut off without fail.

7 Claims, 16 Drawing Sheets

(56) References Cited

FOREIGN PATENT DOCUMENTS

| | | |
|---|---|---|
| JP | 2010-099208 A | 5/2010 |
| JP | 2010-522040 A | 7/2010 |
| WO | WO 2008116095 A1 | 3/2008 |

* cited by examiner

SURGICAL INSTRUMENT

This application is a continuation of application Ser. No. 14/238,117 filed Feb. 10, 2014.

BACKGROUND OF THE INVENTION

Field of the Invention

The present invention relates to a surgical instrument.

Description of the Conventional Art

As is well known, since glaucoma is one of main diseases for an eye, and may cause blindness, proper medical treatment is indispensable. The glaucoma comes about in the case that pressure in the eye maintains an abnormally high numerical value over the long term, and an increase of the pressure in the eye is caused by deterioration of an outflow of aqueous humor. Therefore, a medical treatment for appropriately making the aqueous humor outflow is applied to the glaucoma.

As a medical treatment method of the glaucoma, there is a prescription of a drag (dye drops and oral medication), however, there is also a surgical procedure. Since abnormality in the trabecular meshwork causes deterioration of the outflow of the aqueous humor, there is an operation for removing the trabecular meshwork as the surgical procedure. An instrument for the operation is proposed in the following patent document 1.

Prior Art Document

Patent Document

Patent Document 1: Japanese Unexamined Patent Application Publication (Translation of PCT Application) No. 2002-541975

SUMMARY OF THE INVENTION

Problem to be Solved by the Invention

Since an instrument for incising the trabecular meshwork described in patent document 1 has a flexible construction as a whole including a leading end portion which cuts off the trabecular meshwork, the instrument may have an operability which is not high. Further, in the cutting operation of the trabecular meshwork, there is demanded a function of securely preventing the cutting of a portion which should not be cut off, as well as appropriately cutting a portion to be cut off. However, in the instrument described in the patent document 1, a structure for preventing the cutting of the portion which should not be cut off is deemed to be indefinite.

Accordingly, an object to be solved by the present invention is to provide an instrument for an ophthalmic operation which is excellent in an operability and can securely prevent cutting of a part which should not be cut off.

Means for Solving the Problem

In order to achieve the object mentioned above, a surgical instrument according to the present invention is a surgical instrument used in a cutting operation of a trabecular meshwork, the surgical instrument comprising:

a grasping portion which a practitioner grasps; and a probe which is arranged so as to extend like a rod from an end portion of the grasping portion and has a high rigidity, wherein the probe comprises:

an outflow port which flows out a cleaning liquid toward the trabecular meshwork corresponding to a cut position;

a suction port which is formed in a side surface of the probe, collects the cleaning liquid flowed out of the outflow port as a waste liquid, and sucks the trabecular meshwork into an inner portion of the probe;

a cutting portion which cuts the trabecular meshwork sucked into the suction port; and a protection portion which is arranged closer to a leading end side of the probe than the suction port and the cutting portion, has such a shape as to be extended to a side surface forming the suction port in the leading end of the probe, and protects an outer wall of a canal of Schlemn corresponding to a non-cut position from the cutting and the suction by being positioned between the cutting portion and the outer wall of the canal of Schlemn during the cutting of the trabecular meshwork by the cutting portion, and wherein the surgical instrument further comprises:

a first delivery portion which is connected to a power supply portion for cutting a vitreous body in a vitreous body cutting device transmitting power in a vitreous body cutting operation and carrying out the delivery of the cleaning liquid and the collection of the waster liquid, and is provided for feeding the power for cutting from the device to the cutting portion;

a second delivery portion which is connected to a cleaning liquid supply portion for cutting the vitreous body in the vitreous body cutting device, and is provided for feeding the cleaning liquid from the vitreous body cutting device to the outflow port; and a third delivery portion which is connected to a suction portion for cutting the vitreous body in the vitreous body cutting device, and is provided for feeding the waste liquid sucked by the suction port and the cut trabecular meshwork to the vitreous body cutting device.

As a result, the surgical instrument according to the present invention serves as the ophthalmic surgical instrument which has the probe having the high rigidity and being excellent in the operability and cuts off the trabecular meshwork, and is provided with the protection portion which protects the outer wall of the canal of Schlemn from the cutting and the suction by being positioned between the cutting portion and the outer wall of the canal of Schlemn during the cutting of the trabecular meshwork, in the leading end side of the probe. Therefore, it is possible to securely suppress the cutting of the outer wall of the canal of Schlemn while securely cutting off the trabecular meshwork. Accordingly, it is possible to achieve the surgical instrument which can effectively carry out the surgical procedure in relation to the glaucoma. Further, since the suction port adjacent to the cutting portion is arranged in the side surface of the probe and the protection portion is formed so as to be extended to the side surface forming the suction port in the leading end of the probe, the trabecular meshwork can be cutoff, for example, by inserting the probe into the canal of Schlemn, and it is possible to securely protect the outer wall of the canal of Schlemn at the position facing to the leading end of the probe from the cutting and the suction by the protection portion, according to the simple structure mentioned above. Further, it is possible to execute the trabecular meshwork cutting operation in relation to the glaucoma patient by connecting the surgical instrument according to the present invention to the device for the vitreous body cutting operation. As a result, it is possible to achieve a remarkable effect of contributing to a system simplification, a space saving and a cost reduction in a medical treatment, by using the device both as the device of the system for cutting the vitreous body and the device of the system for cutting the trabecular meshwork, which have been conventionally constructed independently.

Further, an inner tube portion arranged so as to have a longitudinal axis in common may be provided in an inner portion of the probe, and the cutting portion may have a cutting blade which is formed in a side surface of the inner tube portion and cuts the cut position on the basis of a relative rotating motion or a relative translational motion of the inner tube portion in relation to the probe.

According to the invention, since the relatively movable inner tube portion is provided in the inner portion of the probe, and the cutting blade provided in the inner tube portion achieves the cutting function on the basis of the relative motion of the inner tube portion, a mechanism of moving the cutting blade is formed by the simple structure while utilizing a cylindrical shape of the probe. As a result, it is possible to effectively cut while sucking the cut position.

Further, a surgical instrument according to the present invention is a surgical instrument used in a cutting operation of a trabecular meshwork, the surgical instrument comprising a probe,
wherein the probe comprises:
an outflow port which flows out a cleaning liquid toward the trabecular meshwork corresponding to a cut position;
a suction port which is formed in a side surface of the probe, collects the cleaning liquid flowed out of the outflow port as a waste liquid, and sucks the trabecular meshwork into an inner portion of the probe;
a cutting portion which cuts the trabecular meshwork sucked into the suction port; and
the probe having a high rigidity, and
wherein the probe comprises:
an attaching portion for attaching the surgical instrument;
a protection portion which is arranged closer to a leading end side of the probe than the suction port and the cutting portion, has such a shape as to be extended to a side surface forming the suction port in the leading end of the probe, and protects an outer wall of a canal of Schlemn corresponding to a non-cut position from the cutting and the suction by being positioned between the cutting portion and the outer wall of the canal of Schlemn during the cutting of the trabecular meshwork by the cutting portion; and
an adjusting portion which adjusts a distance between the protection portion and the suction port in a state of being attached to the probe by the attaching portion.

As a result, the surgical instrument according to the present invention can be used by being attached, for example, to the existing ophthalmic surgical instrument, on the basis of the structure having the protection portion and the attaching portion. Therefore, it is possible to achieve a remarkable effect of contributing to a great cost reduction in the ophthalmic operation. Further, since the distance between the protection portion and the suction port can be adjusted, it is possible to contribute to an appropriate operation by adjusting to a distance which is suitable for the ophthalmic operation to be carried out. For example, in the case that the instrument is used in a removing operation of the trabecular meshwork applied to the glaucoma patient, the position of the suction port can be aligned with the position of the trabecular meshwork to be cut off in a state in which the protection portion goes into the canal of Schlemn. Therefore, it is possible to carry out the appropriate trabecular meshwork cutting operation.

Figure 1:
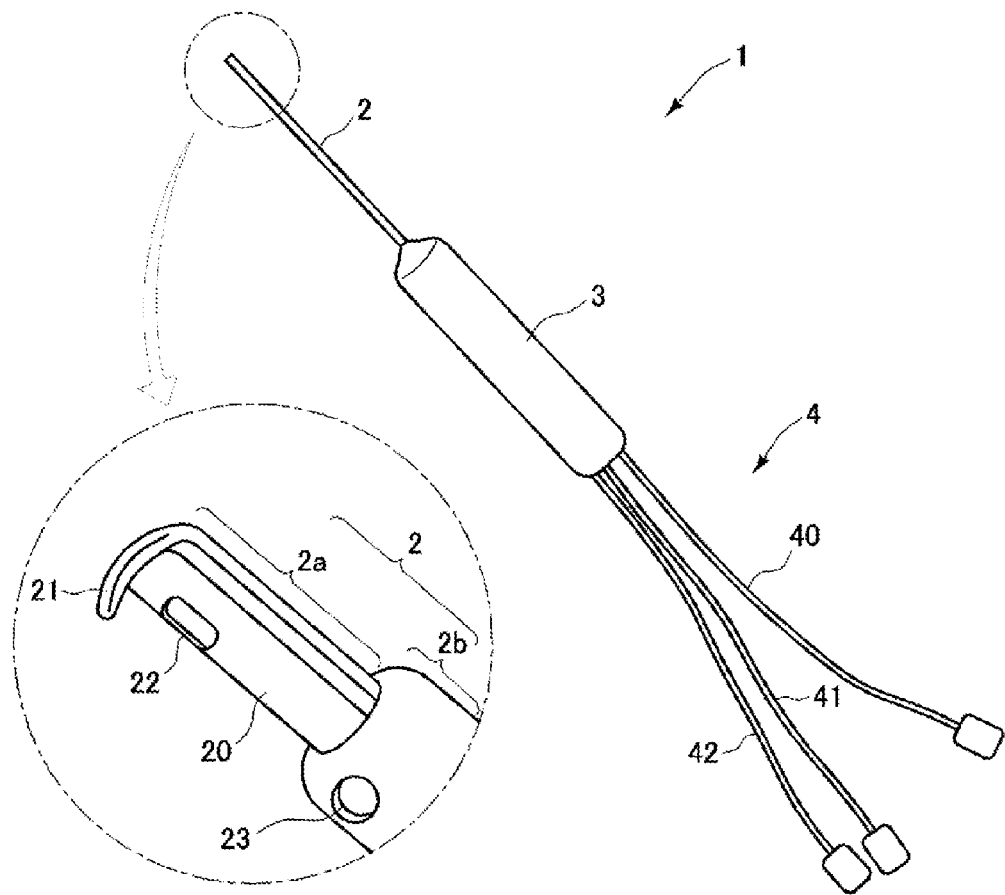
FIG. 1 is a view showing a surgical instrument in a first practical example according to the present invention.

DESCRIPTION OF REFERENCE NUMERALS 1 surgical instrument
2 probe
3 body portion (grasping portion)
4 cable and tube portion
40 electric power cable (first delivery portion)
40' air tube (first delivery portion)
41 cleaning liquid tube (second delivery portion)
42 waste liquid tube (third delivery portion)

DETAILED DESCRIPTION OF PREFERRED EMBODIMENTS

A description will be given below of a practical example according to the present invention with reference to the accompanying drawings. First of all, FIG. 1 shows a surgical instrument 1 (hereinafter, refer to as an instrument) in a practical example of the present invention. The instrument 1 is an instrument which is used for cutting off, particularly, a trabecular meshwork in a glaucoma operation, and is provided with a probe 2, a body portion 3 and a cable and tube portion 4.

The probe 2 is a region which extends from a leading end side of the body portion 3 and is inserted into an eye of a patient. The probe has a cylindrical shape which is formed linearly from the body portion 4, and is constructed by a small diameter portion 2a which is positioned in a leading end side and has a smaller diameter, and a large diameter portion 2b closer to the body 3, as is shown by an enlarged portion surrounded by a one-dot chain line. The diameter of the probe 2 (the small diameter portion 2a and the large diameter portion 2b) may be set to a numerical value which is suitable for cutting off the trabecular meshwork.

The small diameter portion 2a of the probe 2 is structured, as shown in FIG. 1, such that a hole portion 20 is formed in a side surface in the vicinity of a leading end of a cylinder portion 20 having a cavity in its inner portion, and a protection portion 21 is provided in an inverse side surface to the hole portion 20 and a leading end surface side of the hole portion 20. An inner portion of the cylinder portion 20 is connected to a suction mechanism as mentioned later, and a part of the trabecular meshwork is sucked into the inner portion of the hole portion 20. A cutter (a cutting portion) is provided in the inner portion of the hole portion 20, and the sucked trabecular meshwork is cut by the cutter and is sucked into the body portion 3. A cleaning liquid soiled by an operation is also sucked into the body portion 3 from the hole portion 20.

The large diameter portion 2b of the probe 2 is provided with a hole portion 23 in a side surface in the vicinity of a leading end of the large diameter portion. The hole portion 23 is connected from a region supplying the cleaning liquid, and the cleaning liquid flows out (jets out or injects out) toward a probe leading end direction, that is, toward the periphery of a treatment position; from the hole portion 23 at the operating time. A material of the probe 2 may be set, for example, to a metal or a resin having a high rigidity.

The body portion 3 (a grasping portion) is a region which a practitioner grasps at the operating time, is formed, for example, as a tubular shape which is suitable for grasping, and is provided in its inner portion with a driving portion driving the cutting portion (mentioned later). Further, the cut trabecular meshwork, the cleaning liquid and the soiled waster liquid are fed from the probe (or to the probe) through the inner portion of the body portion 3.

The cable and tube portion 4 extends from a rear end side of the body portion 3 and has relations with an electric power supply, a cleaning liquid supply, a cut position and a waste liquid collection. The cable and tube portion 4 may be provided with a plurality of cables or tubes, for example, may be provided with three cables or tubes constituted by an electric power cable 40, a cleaning liquid (cleaning fluid) supply tube 41 and a waste liquid tube 42 (or four cables or tubes in the case that both polar lines of the electric power cable 40 are respectively counted), as shown in FIG. 1.

The electric power cable 40 supplies an electric power for a cutting process in the leading end of the probe 2 as mentioned later. The cleaning liquid supply tube 41 is a tube for feeding the cleaning liquid to the treatment portion during the cutting treatment of the trabecular meshwork. The waste liquid tube 42 is a tube for collecting and disposing of the cut trabecular meshwork, the soiled waste liquid after cleaning the treatment portion and bloody issue from the operation region.

Figure 2:
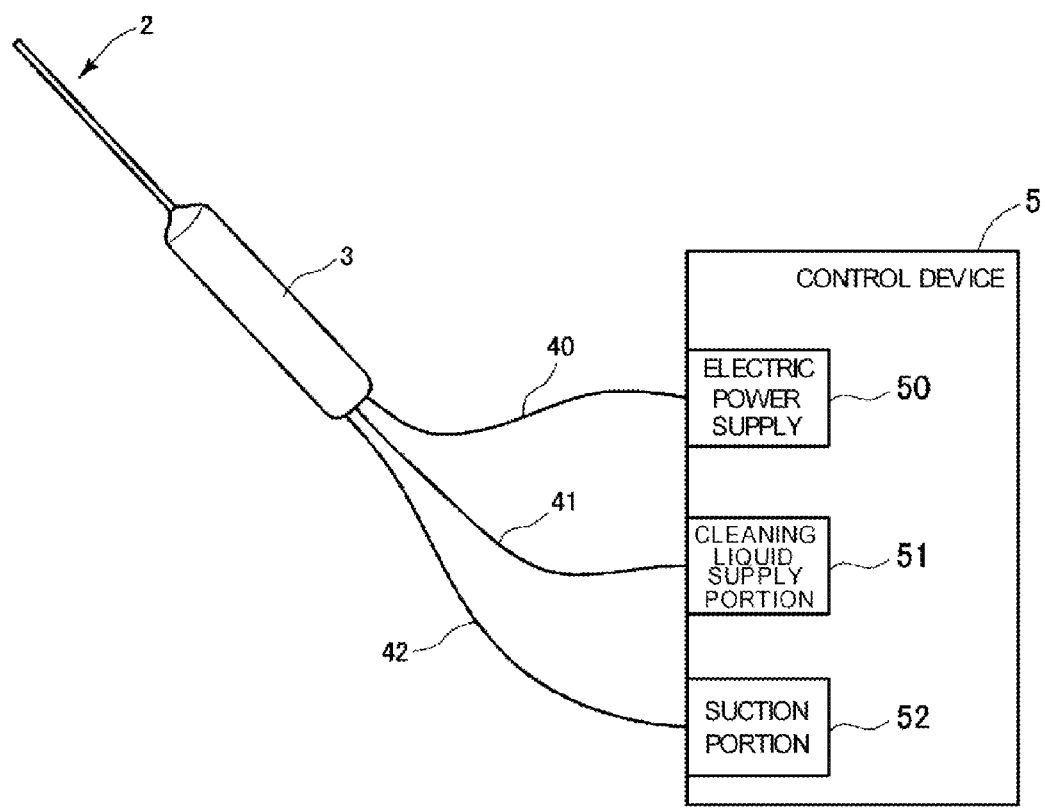
FIG. 2 is a view showing a state of being connected to a control device.

The instrument 1 is used by being connected to a control device 5 at the operating time, as shown in FIG. 2. The control device 5 is provided with an electric power supply 50 (an electric power supply portion), a cleaning liquid supply portion 51 and a suction portion 52, as a main construction. The electric power supply 50 supplies an electric power to the instrument 1 by being connected to the electric power cable 40 of the instrument 1. On the basis of the supplied electric power, the instrument 1 drives the cutting portion. The electric power supply 50 may be structured such as to convert a commercial power into an electric power suitable for the instrument 1 (for example, a relatively lower electric voltage value) so as to supply to the instrument 1. The cleaning liquid supply portion 51 supplies the cleaning liquid to the instrument 1 by being connected to the cleaning liquid tube 41 of the instrument 1. The suction portion 52 sucks the waste liquid and the cut position through the instrument 1 by being connected to the waste liquid tube 42 of the instrument 1.

FIGS. 3 to 8 are cross sectional views showing a detailed structure in a plurality of embodiments of the instrument 1. A description will be given of a structure and a motion of the instrument 1 in each of the embodiments with reference to these drawings. FIGS. 3 to 8 are schematic views, and a length in a vertical direction of the drawing is compressed, for example.

Figure 3:
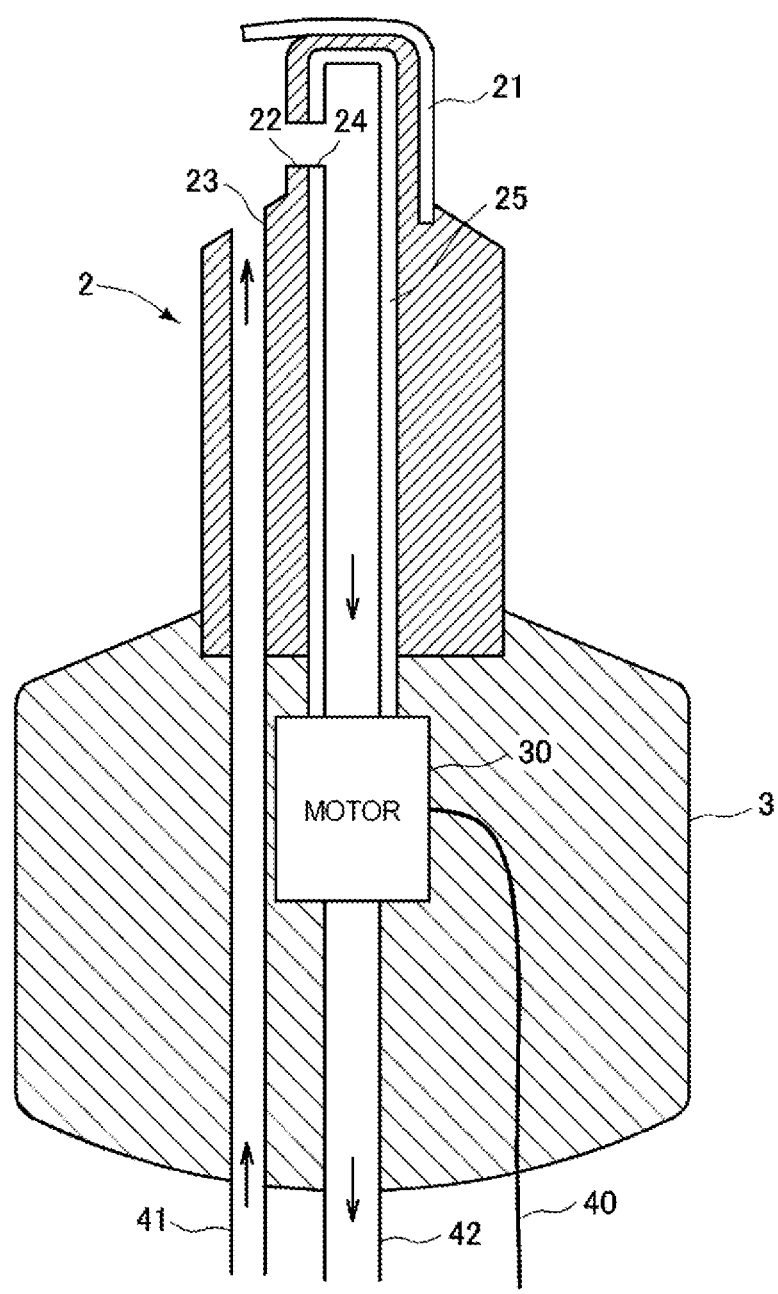
FIG. 3 is a view showing a first embodiment of the surgical instrument according to the present invention.

First of all, FIG. 3 shows an axial cross sectional view of the probe 2 and the body portion 3 in a first embodiment. As is shown in the drawing, the probe 2 is provided with an inner tube portion 25 (an inside cylinder portion) in an inner side of an outer tube portion (an outside cylinder portion), the outer tube portion being constructed by the cylinder portion 20 shown in FIG. 1. The inner tube portion 25 is arranged so as to be relatively movable in relation to the outer tube portion (the cylinder portion 20).

Then inner tube portion 25 is formed as a cylindrical shape having a cavity in its inner portion, and a hole portion 24 is also formed in the inner tube portion 25 at a position which laps over an inside of the hole portion 22 of the outer tube portion 20 according to a positional relationship in FIG. 3. A passage formed in the inner portion of the inner tube portion 25 is connected to the waste liquid tube 41 from the hole portion 24. The protection portion 21 is arranged over a right side and an upper side in the drawing of the outer tube portion 20. The protection portion 21 may be formed, for example, as a plate shape which is bent along an outer shape of the outer tube portion 20.

As shown in FIG. 3, the probe 2 may be structured, for example, such as to be inserted into a hole portion formed in the body portion 3 so as to be fixed. Further, the protection portion 21 may be structured, for example, such as to be inserted into a hole portion formed in a taper portion on the boundary between the small diameter portion 2a and the large diameter portion 2b so as to be fixed. In FIG. 3, the cylinder portion 20 (the outer tube portion) is formed integrally with the large diameter portion 2b, however, the cylinder portion 20 (the outer tube portion) may be structured such as to be formed independently from the large diameter portion 2b and be inserted into the large diameter portion 2b.

A passage for the cleaning liquid is formed in the taper portion on the boundary between the small diameter portion 2a and the large diameter portion 2b, the passage passing through the hole portion 23, further passing through the body portion 3 to the cleaning liquid tube. The cleaning liquid is supplied from the cleaning liquid supply portion 51 of the control device 5 together with an appropriate water pressure, and passes through the body portion 3 and the probe 2 so as to be jetted out to the periphery of the operation region from the hole portion 23.

In the case that the hole portion 22 and the hole portion 24 come to the overlapping positional relationship at the operating time, the trabecular meshwork in the vicinity of the hole portions 22 and 24 (a part of all the trabecular meshwork) is sucked into the inner portions of the hole portions 22 and 24 on the basis of the suction of the suction portion 52 in the control device 5. At the same time, the cleaning liquid cleaning the operation region is sucked into the hole portions 22 and 24.

Figure 4:
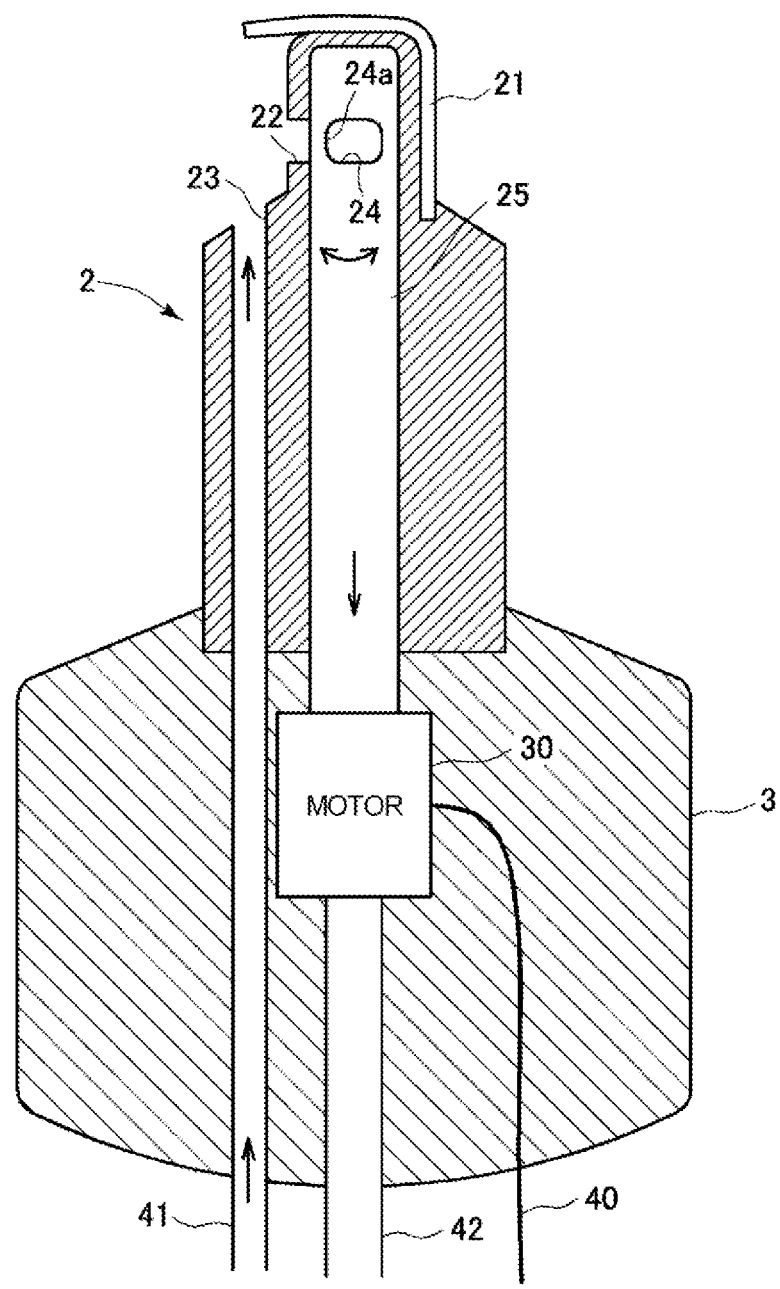
FIG. 4 is a view showing a state in which an inner tube portion rotates in the first embodiment.

In an embodiment in FIG. 3, a motor 30 is equipped in the body portion 3. The motor 30 is arranged at the center position of the body portion 3 so as to have an axis of rotation in common with the axis of the probe 2. Further, the motor 30 is supplied the electric power from the control device 5 through the electric power cable 40, and makes the inner tube portion 25 carry out a rotary motion around the axis of the probe 2. FIG. 4 shows a state in which the inner tube portion 25 rotates at about 90 degrees.

A cutter 24a is formed in an end portion (for example, an end portion in a lateral direction of the drawing) of the hole portion 24 of the inner tube portion 25, and the inner tube portion 25 rotates in relation to the outer tube portion 20, whereby the trabecular meshwork sucked into the hole portions 22 and 24 as mentioned above is cut by the cutter 24a. A cutter may be formed in the hole portion 22 of the outer tube portion 20. The cut trabecular meshwork and waste liquid pass through the passage within the inner tube portion 25 and further pass through the waste liquid tube so as to be sucked into the suction portion 52. The trabecular meshwork and the waste liquid reserved in the suction portion 52 may be disposed, for example, according to an appropriate method.

Figure 5:
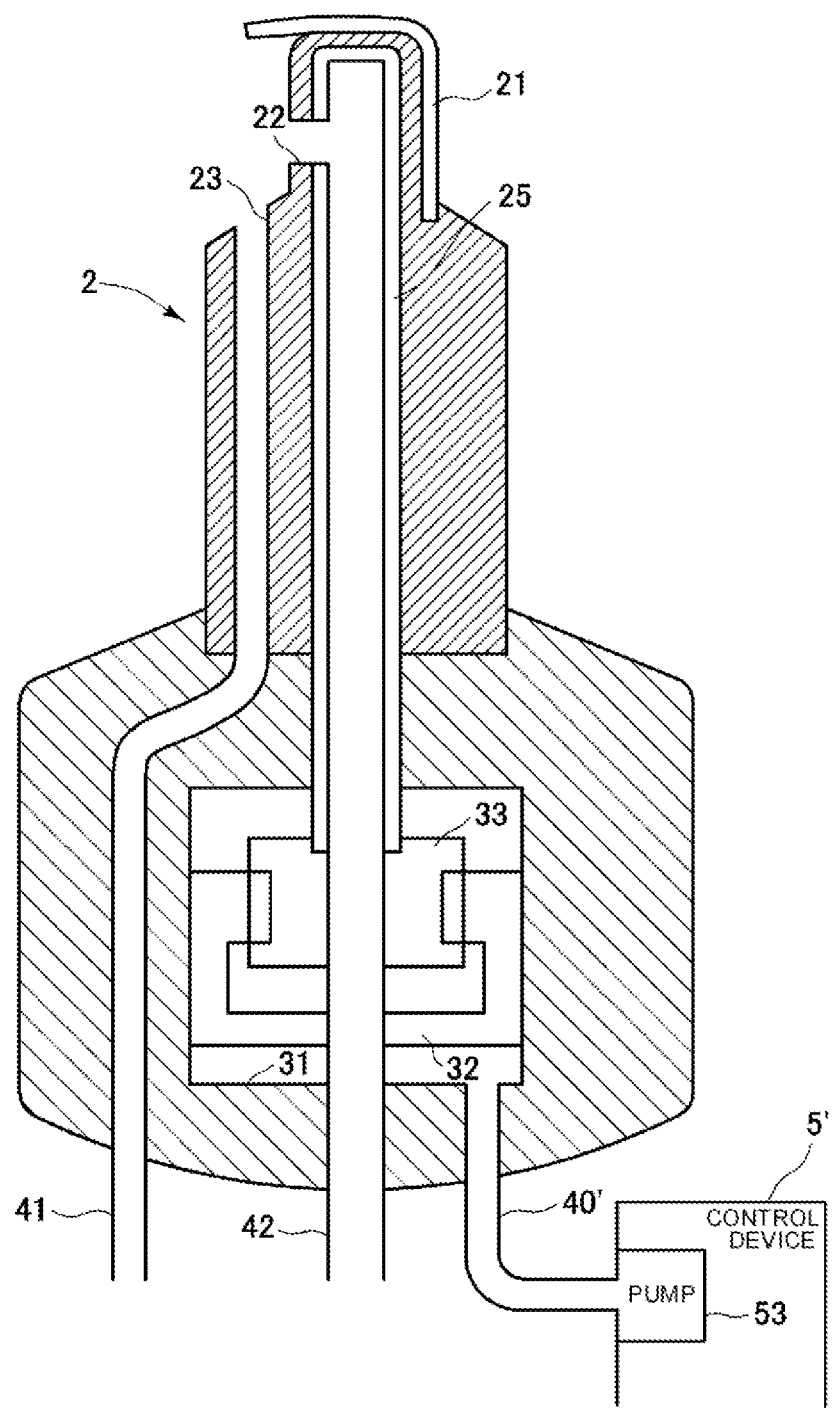
FIG. 5 is a side elevational view showing a second embodiment of the surgical instrument according to the present invention.

Next, FIG. 5 shows the other embodiment of the instrument 1. In the embodiment in FIGS. 5 to 8, regions denoted by the same reference numerals as those of FIGS. 3 and 4 denote the same regions, and an overlapping description will be omitted.

In the embodiment in FIG. 5, a mechanism of an air cylinder is equipped in place of the motor 30. Further, a control device 5' is equipped with a pump 53 in place of the electric power supply portion 50. Further, the instrument 1 is equipped with an air tube 40' for supplying air serving as a power in place of the electric power cable 40. The instrument is formed a cylinder 31 within the body portion 3, and is provided with a piston 32 and a screw portion 33.

The cylinder 31 is formed as a cylindrical shape which has an axis in common with the probe 2, and the piston 32 is arranged within the cylinder 31 so as to be movable in an up and down direction in the drawing. A thread groove is formed in the piston 32, and is threadably fitted to a thread groove of the screw portion 33. The screw portion 33 is fixed to the inner tube portion 25.

In the structure mentioned above, in the case that the supply and suction of the air serving as the power are repeated from the pump 53 of the control device 5', the piston 32 moves up and down, the up-and-down motion is converted into a rotary motion of the screw portion 33 by a screw mechanism between the piston 32 and the screw portion 33. The inner tube portion 25 rotates on the basis of the rotary motion of the screw portion 33. As a result, the cutter 24a of the hole portion 24 of the inner tube portion 25 cuts the trabecular meshwork sucked into the hole portion 24.

Figure 6:
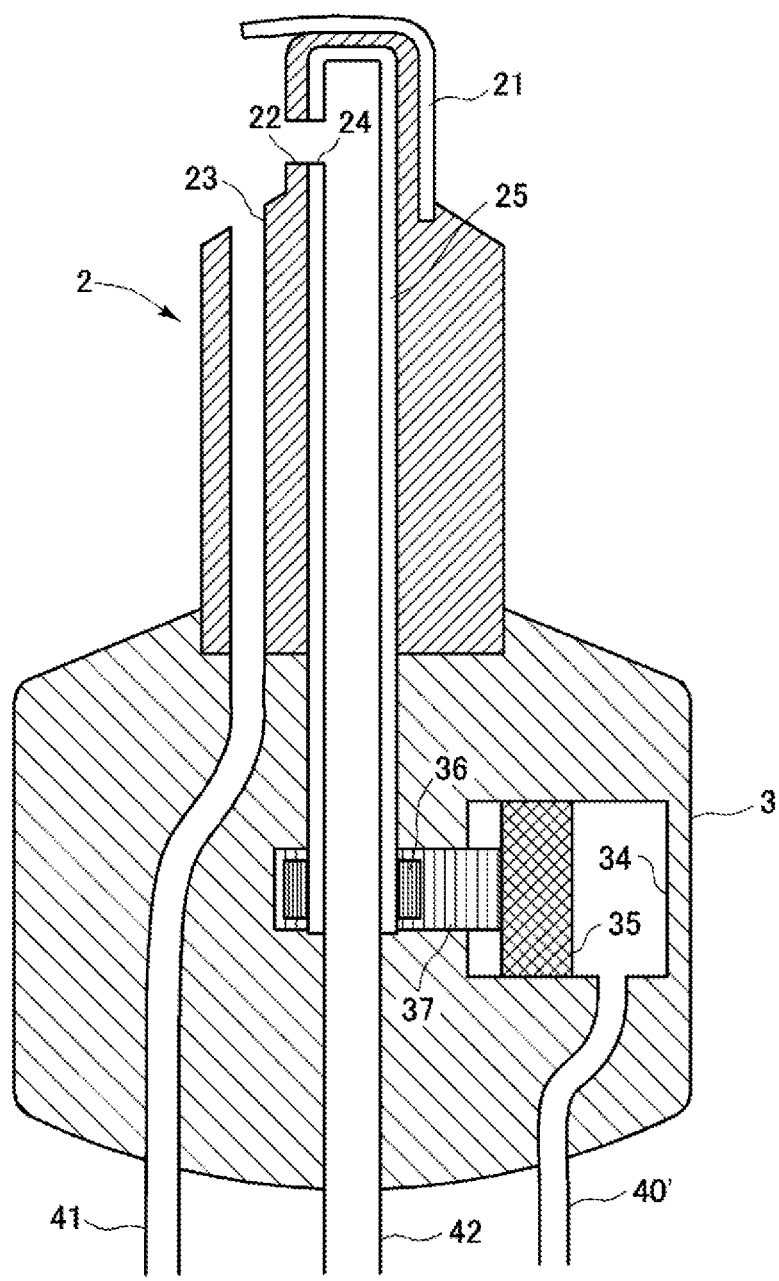
FIG. 6 is a side elevational view showing a third embodiment of the surgical instrument according to the present invention.

Next, FIG. 6 shows a third embodiment of the instrument 1. The embodiment is also provided with the air cylinder structure. Specifically, the instrument 1 is formed a cylinder 34 within the body portion 3, and is provided with a piston 35, a gear 36 and a rack 37. The cylinder 34 is formed as a cylindrical shape in which an axial direction of the cylinder 34 is orthogonal to the axial direction of the probe 2, and the piston 35 is arranged within the cylinder 34 so as to be movable in a lateral direction in the drawing. The rack 37 is fixed to the piston 35, and moves to the right and left integrally with the piston 37. The gear 36 forms a cam mechanism between the gear 36 and the rack 37, and converts a translational motion of the rack 37 into the rotary motion. The gear 36 is fixed to the inner tube portion 25.

According to the structure mentioned above, in the instrument 1, in the case that the supply and the suction of the air serving as the power are repeated from the pump 53 of the control device 5', the piston 32 moves to the right and left in the drawing, the rack 37 moves to the right and left integrally with the piston, and the lateral motion is converted into the rotary motion of the gear 36 by the cam mechanism between the rack 37 and the gear 36. The inner tube portion 25 rotates on the basis of the rotary motion of the gear 36. As a result, the cutter 24a of the hole portion 24 in the inner tube portion 25 cuts the trabecular meshwork sucked into the hole portion 24.

The rotary motion of the inner tube portion 25 in FIGS. 3 and 4 is a rotary motion having a fixed speed in the same direction, and in the rotary motion of the inner tube portion 25 in FIGS. 5 and 6, the rotation with a predetermined rotating angle width in forward and backward directions may be repeated.

Figure 7:
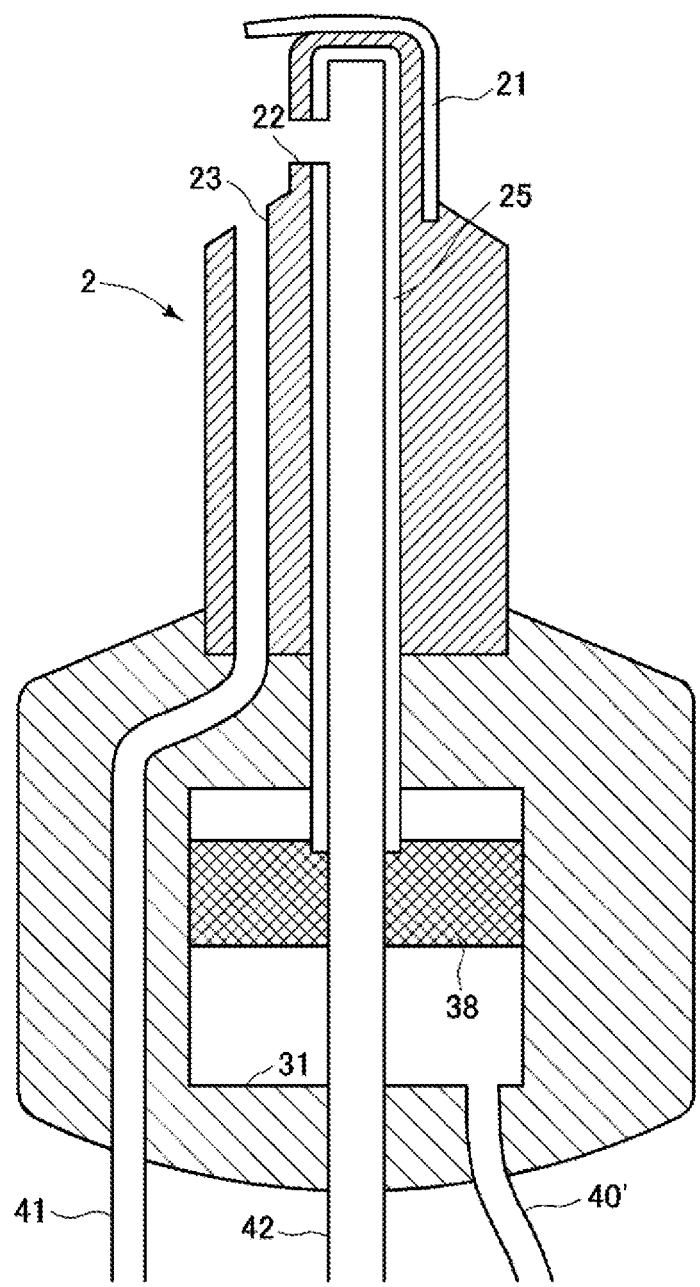
FIG. 7 is a side elevational view showing a fourth embodiment of the surgical instrument according to the present invention.
Figure 8:
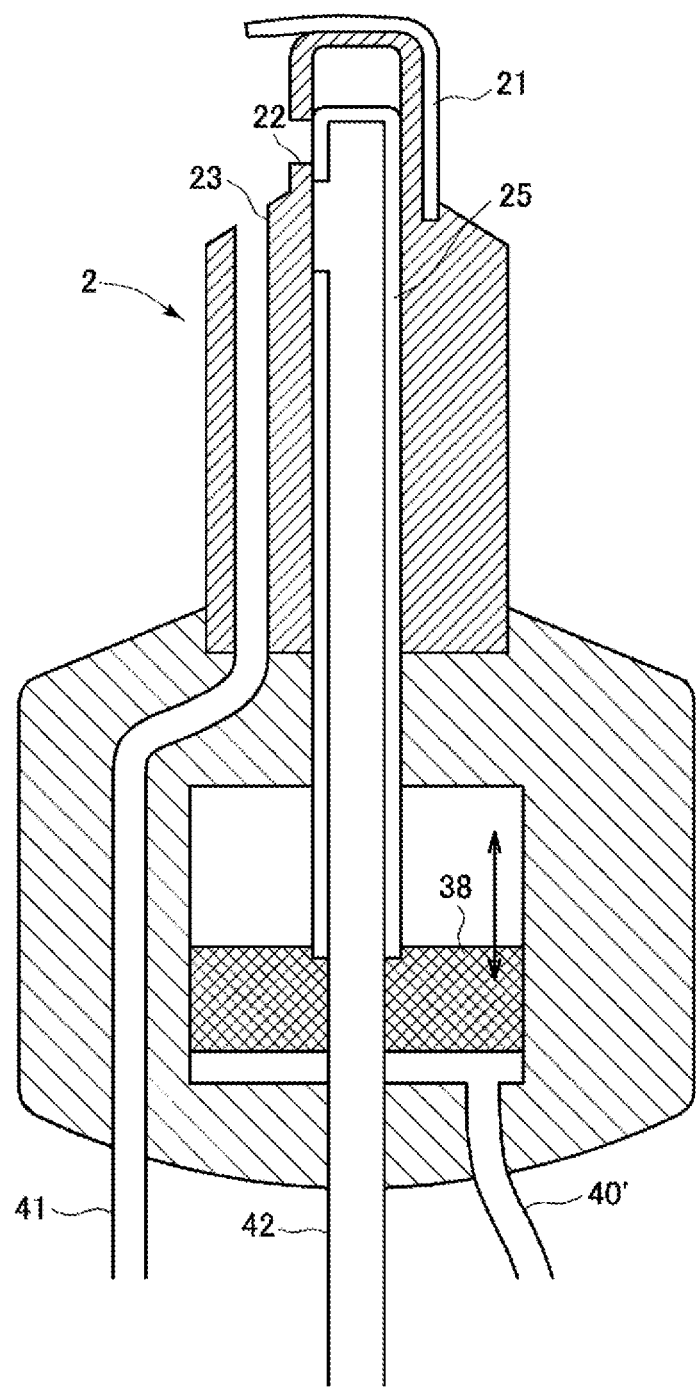
FIG. 8 is a view showing a state in which an inner tube portion moves in the fourth embodiment.

Next, FIGS. 7 and 8 show a fourth embodiment of the instrument 1. In the embodiment, the inner tube portion 25 moves in parallel in a vertical direction of the drawing. Specifically, the instrument 1 is formed the cylinder 31, and is provided with a piston 38. The cylinder 31 is formed as a cylindrical shape which has an axis in common with the probe 2, and the piston 38 is arranged within the cylinder 31 so as to be movable in a vertical direction in the drawing. The piston 38 is fixed to the inner tube portion 25.

In the structure mentioned above, in the case that the supply and the suction of the air serving as the power are repeated from the pump 53 of the control device 5', the piston 38 moves up and down in the drawing. The inner tube portion 25 moves up and down on the basis of the up-and-down motion of the piston 38. FIG. 8 shows a state in which the inner tube portion 25 moves downward in the drawing. On the basis of the downward movement of the inner tube portion 25, the cutter 24a of the hole portion 24 in the inner tube portion 25 cuts the trabecular meshwork sucked into the hole portion 24.

In the embodiment, the cutter 24a may be formed in an upper end portion in the hole portion 24 of the inner tube portion 25. Alternatively, it is preferable to make a moving distance of the inner tube portion 25 longer, form the cutter 24a in both upper and lower end portions in the hole portion 24 of the inner tube portion 25, and cut the trabecular meshwork by both the upper and lower cutters 24a. Of course, the cutter may be provided in the hole portion 22 of the outer tube portion 25.

Figure 9:
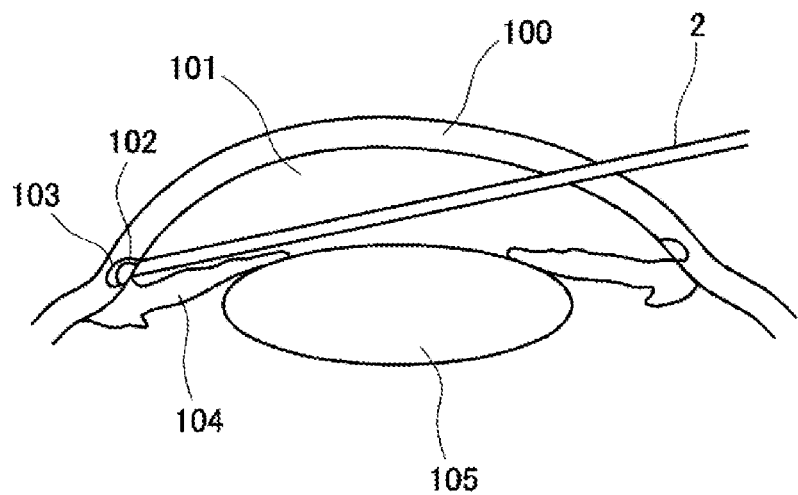
FIG. 9 is a view showing an example of a condition of a glaucoma operation using the surgical instrument according to the present invention.

The instrument 1 having the structure mentioned above is used in the cutting work of the trabecular meshwork in the surgical procedure of the glaucoma. Describing with reference to a schematic view of an eye structure shown in FIG. 9, an aqueous humor is created in a ciliary body positioned in a lower portion of the drawing of an iris 104 of the eye.

Normally, the aqueous humor advances on a crystalline lens 105 and thereafter flows out of a corner I a peripheral direction of an anterior chamber of eye 101. The trabecular meshwork 102 and the canal of Schlemn 103 exist in the corner. The trabecular meshwork 102 serves as a filter which restricts the outflow of the aqueous humor. The canal of Schlemn 103 has a structure for the aqueous humor flowing out.

In the case that the trabecular meshwork 102 abnormally deforms or generates a functional abnormality, the flow of the aqueous humor getting out of the anterior chamber of eye 101 is restricted. As a result, the pressure in the eye is abnormally increased, and the glaucoma is generated. The surgical instrument 1 according to the present invention is an effective instrument in a surgical procedure in relation to the glaucoma. One example of the operating method using the instrument 1 is as follows.

Figure 10:
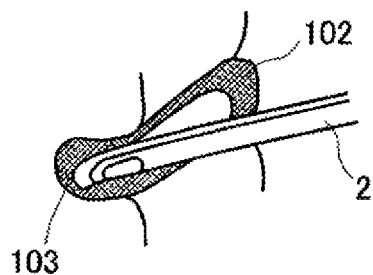
FIG. 10 is an enlarged view of FIG. 9.

In preparation of the operation, a head position of a patient is decided as well as a microscope is inclined to a practitioner side at 30 degrees to 45 degrees so that the trabecular meshwork can be seen from a front face through a gonioscope. After incising a corner by a knife (for example, 1.7 mm) and evacuating the aqueous humor a little, a visco-elastic material is injected. In order to easily view, the visco-elastic material may be preferably filled particularly in the corner portion. After putting the gonioscope and confirming the trabecular meshwork, the probe 2 is inserted into the canal of Schlemn 103 and the cutting is started. As shown in FIG. 10, the instrument 1 is moved toward the side in which the hole portion 21 is formed, within the canal of Schlemn 103. At this time, the direction in which the instrument 1 moves forward is identical to the direction in which the protection portion 21 is extended.

In the case that the cutting is advanced in a clockwise direction and is advanced thereafter in a counterclockwise direction, it is possible to cut off from 90 degrees to 120 degrees. (In the case that a cataract operation is simultaneously carried out, a cornea incision wound of 1.7 mm is expanded to 3.0 mm here and the lens is inserted.) After washing the visco-elastic material and the reflex bloody issue so as to completely remove, the fact that any aqueous humor is not leaked from the wound portion is finally checked. In order to keep the pressure in the eye to some degree, the wound is sutured in a stitch (for example, with 10-0 nylon) as occasion demands.

As an advantage of the operation, for example, there can be listed up a low invasiveness that the incise wound of the cornea 100 is small and the canal of Schlemn is hard to be damaged, and a certainty that the trabecular meshwork can be cut while being actually seen. Further, since a serious complication after the operation is not generated so much, there is a chance of accommodating to the operation more early than the increased number of instillation of drop, as long as the glaucoma has a high pressure in the eye which is equal to or higher than 21 mmHg in the early stage and the middle stage.

As mentioned above, the trabecular meshwork can be cut (curetted) by using the instrument 1 according to the present invention (the expression of trabecular meshwork cut includes the matter that the inner wall of the canal of Schlemn is cut at a predetermined angle range from the anterior chamber side and the trabecular meshwork is exposed). At this time, the outer wall of the canal of Schlemn is protected by the protection portion 21.

Figure 11:
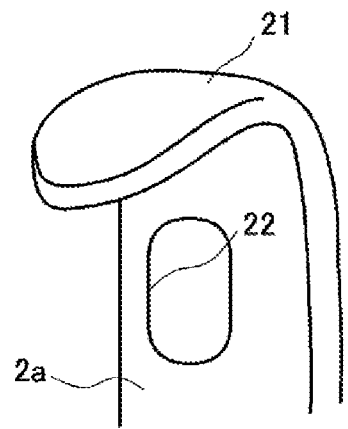
FIG. 11 is a view showing the other practical example of the protection portion.
Figure 12:
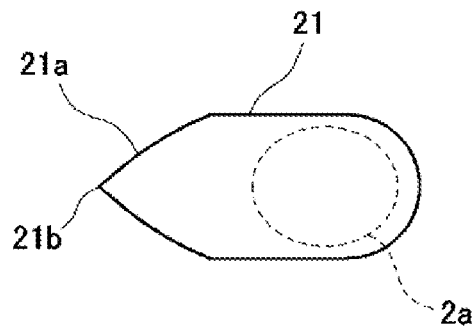
FIG. 12 is a view in the case that FIG. 11 is seen from the above.
Figure 13A:
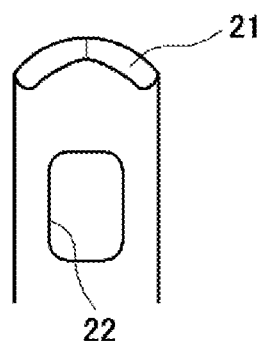
FIG. 13A is a view showing a first example in the case that FIG. 11 is seen from a side of a hole portion.

The protection portion 21 can be formed as various shapes. FIGS. 11 to 13 show a first embodiment of the protection portion 21. FIG. 11 is a perspective view, FIG. 12 is a view in the case that FIG. 11 is seen from the above of the drawing, and FIG. 13A is a view in the case that FIG. 11 is seen from the side of the hole portion 22. The protection portion 21 is arranged so as to come into contact with a side in an inverse side to the side in which the hole portion 22 is formed in the small diameter portion 2a of the probe 2 as mentioned above, is bent along the leading end shape of the probe 2, and is extended approximately in a parallel direction to the leading end surface of the probe 2.

As shown in FIG. 12, a front portion 21a of the protection portion 21 may be formed as a triangular shape (or a tapered shape) (a corner portion may be formed as a curved surface shape). In the shape, since a tip of the protection portion 21 is narrowed toward a forward moving direction in the case that the probe 2 is moved forward along the canal of Schlemn 103 as shown in FIG. 10, the advancing of the probe 2 can be smoothly carried out. As mentioned above, the protection portion 21 also serves as a guide portion for advancing the leading end of the probe along the canal of Schlemn.

Further, as shown in FIG. 12, a leading end 21b of the protection portion 21 may be formed as a sharp shape. The shape is preferable for sticking the leading end 21b of the protection portion 21 into the trabecular meshwork so as to advance the probe in the case that the leading end of the probe is advanced into the trabecular meshwork at the first time of the operation.

Figure 13B:
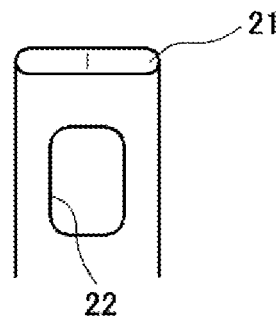
FIG. 13B is a view showing a second example in the case that FIG. 11 is seen from the side of the hole portion.

Further, as shown in FIG. 13A, an upper end in the drawing of the protection portion 21 may be formed as a rounded concave shape. As a result, since the upper end is along the lines of the curved surface shape of the canal of Schlemn at the operating time, and does not injure the canal of Schlemn, the structure is preferable. The shape of the upper end of the protection portion 21 may be formed as a chevron concave shape. Alternatively, as shown in FIG. 13B, the upper end in the drawing of the protection portion may be formed as a flat shape. In the present invention, the shape of the upper end in the drawing of the protection portion 21 may be formed as any shape which can play a role of protecting the non-cut portion and serve as a guide portion, without being limited to the examples in FIGS. 13A and 13B.

Figure 15:
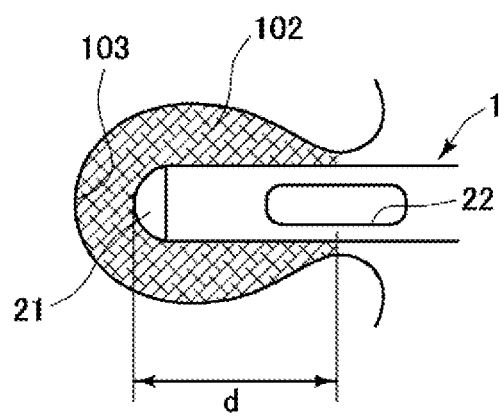
FIG. 15 is an enlarged view of FIG. 10.
Figure 16:
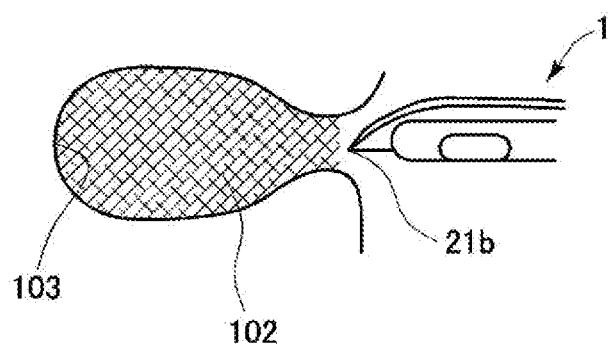
FIG. 16 is a view showing an example of a procedure prior to FIG. 10 in the glaucoma operation.

In the shape of the leading end of the probe, it is important to make a distance from (the upper end of) the protection portion 21 to the hole portion 22 appropriate. As shown in FIG. 15, a distance d from (the upper end of) the protection portion 21 to the hole portion 22 is set so that the hole portion 22 comes to the position of the trabecular meshwork to be cut off, in a state in which the protection portion 21 is in a range after going into the trabecular meshwork until coming into contact with the canal of Schlemn. The position of the trabecular meshwork to be cut off may be set, for example, to include a side near the center of the eye in the trabecular meshwork within the canal of Schlemn (a side in which the probe is inserted into the canal of Schlemn).

The surgical instrument 1 of the glaucoma according to the present invention can exist together with the existing medical treatment device. A mechanism thereof is shown in FIG. 14.

Figure 14:
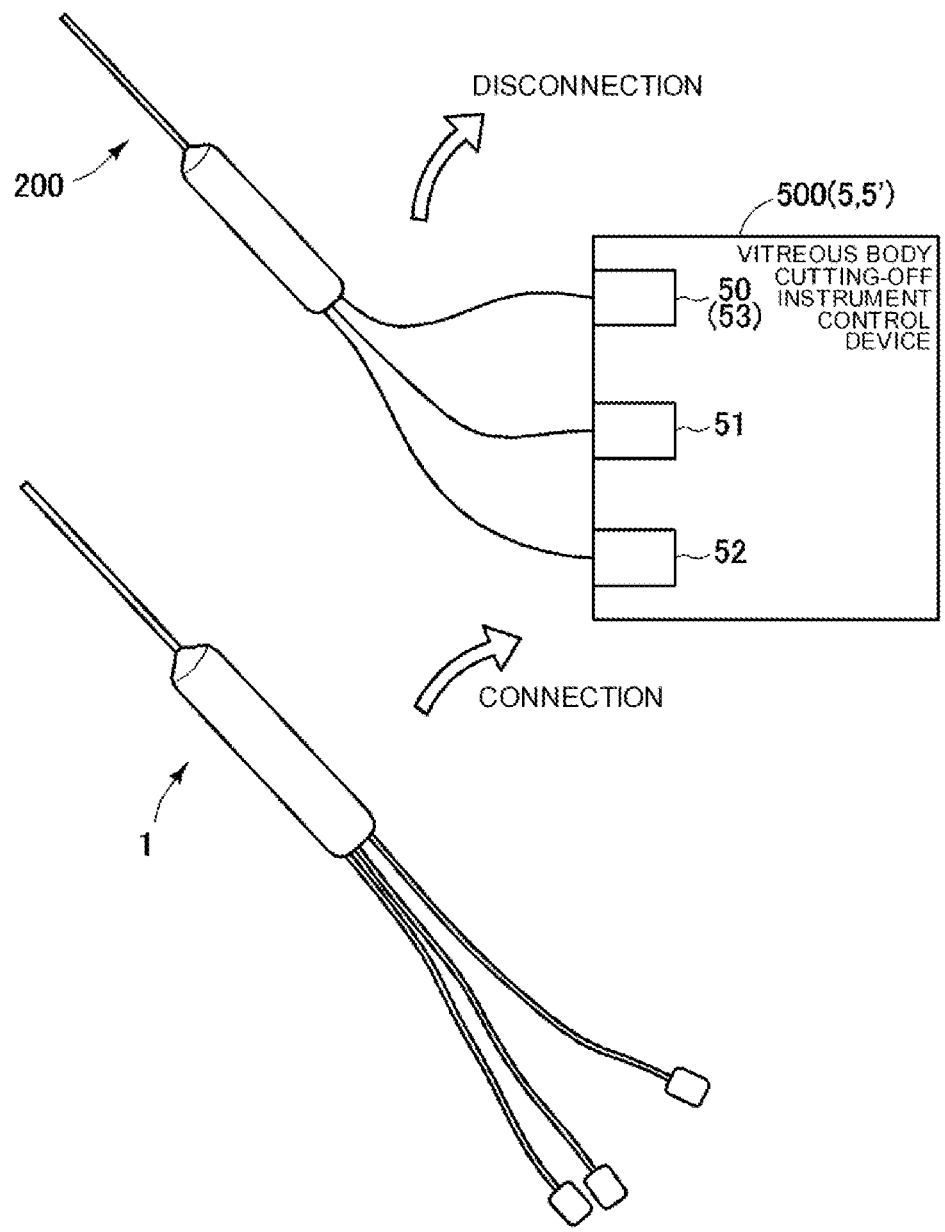
FIG. 14 is a view showing a condition that the surgical instrument according to the present invention is used both the surgical instrument and a vitreous body cutting system.

FIG. 14 shows an operation system for cutting off the vitreous body. The system is provided with a control device 500 for cutting off the vitreous body and an instrument 100 for cutting off the vitreous body. The control device 500 for cutting off the vitreous body is provided with an electric power supply portion 50 (or a pump 53) for cutting off the vitreous body, a cleaning liquid supply portion 51, and a suction portion 52. The instrument 100 for cutting off the vitreous body is provided with cables or tubes. By connecting the cables or the tubes to the electric power supply portion 50 (or the pump 53), the cleaning liquid supply portion 51 and the suction portion 52, an electric power driving a cutter for cutting off the affected area (the vitreous body) is supplied to a cutting portion of the instrument 100 for cutting off the vitreous body, the cleaning liquid is supplied to the operation region, and the cut region (the vitreous body) and the waste liquid reflowed from the operation region are sucked and collected. As a result, it is possible to achieve the vitreous body cutting operation using the instrument 100 for cutting off the vitreous body.

According to the knowledge of the inventor, a function required for the control device 5 (5') for cutting off the trabecular meshwork is similar to the function of the existing control device 500 for cutting off the vitreous body, and the control devices can be sufficiently used both as the control device for cutting off the trabecular meshwork and the control device for cutting off the vitreous body. In other words, the control device 5 (5') mentioned above in relation to the instrument 1 according to the present invention can be substituted by the control device 500 for cutting off the vitreous body in FIG. 14. As a result, it is possible to greatly contribute to simplification, space saving and cost reduction of the system in the ophthalmic medical treatment by using the device part both as the device part of the system for cutting off the vitreous body and the device part of the system for cutting off the trabecular meshwork which have been conventionally constructed independently. The device is not limited to the control device 500 for cutting off the vitreous body, but may employ the other device having the same function.

The practical example may be optionally changed within the range of the spirits described in claims. For example, the instrument 1 can be used for the cutting operation of the vitreous body. Since the instrument 1 has the equipment which is necessary for cutting off the vitreous body, the instrument 1 can achieve a high general versatility so as to correspond to both the glaucoma and the vitreous body.

Figure 17:
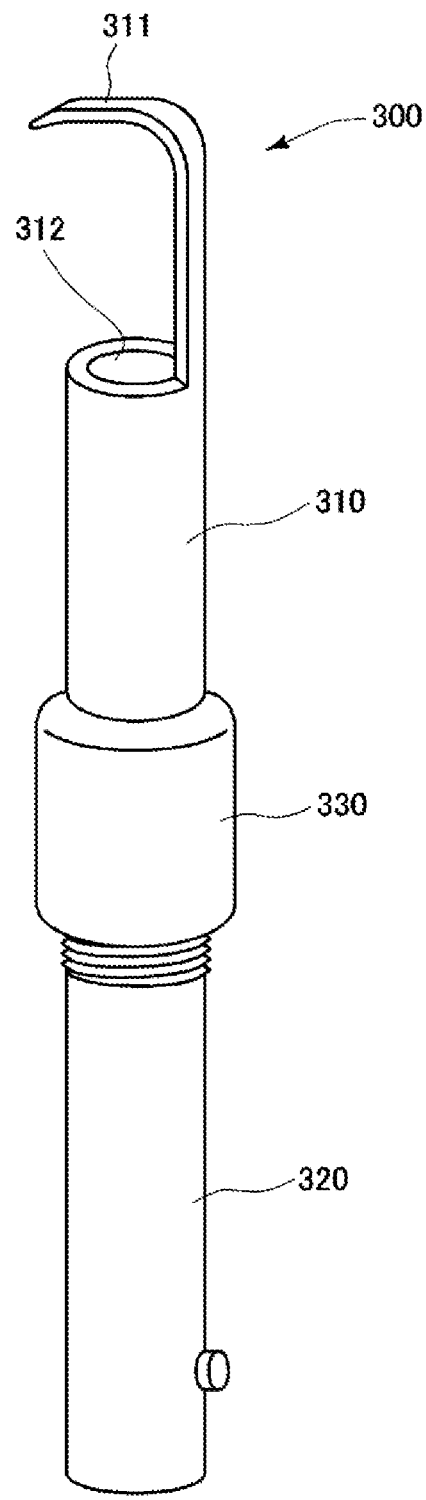
FIG. 17 is a view showing an embodiment of an attaching type of the surgical instrument according to the present invention.

The embodiment mentioned above is structured, as shown in FIG. 1, such that the protection portion 21 is integrated with the other probe 2, body portion 3, and cable and tube portion 4, however, the present invention is not limited to the embodiment mentioned above. FIG. 17 shows a perspective view of an attaching type instrument structured such that only the protection portion is attached. This structure may be attached, for example, to the vitreous body surgical instrument 200 shown in FIG. 14. A description will be given below of the case that the structure is attached to the instrument 200.

Figure 18:
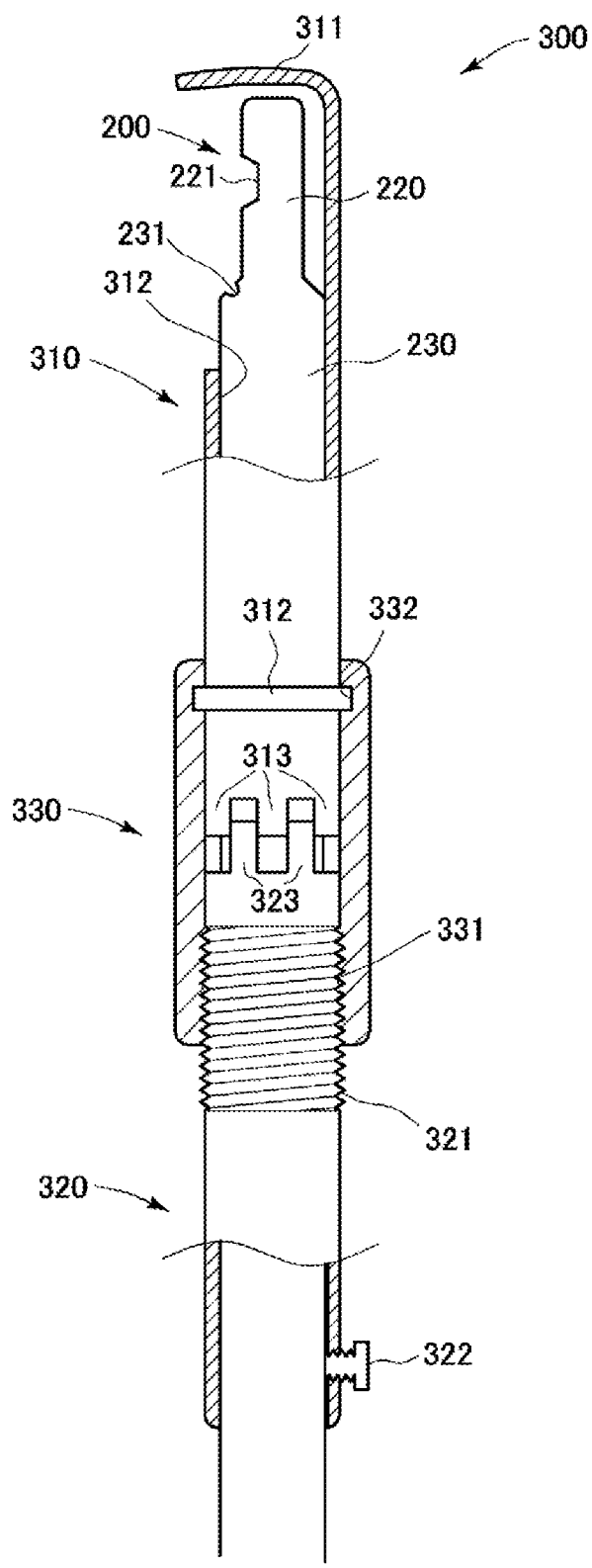
FIG. 18 is a partly cross sectional view of the attaching type surgical instrument.

It is assumed that the instrument 200 has the same structures and shapes as those of the instrument 1 except the structure that the protection portion is not formed. As shown in FIG. 18, a probe of the instrument 200 has a small diameter portion 220 and a large diameter portion 230, a hole portion 221 is formed in the small diameter portion 220, and a hole portion 231 is formed in a taper portion from the large diameter portion 230 to the small diameter portion 220. The cleaning liquid is supplied from the hole portion 231 to the treatment portion. The hole portion 221 is equipped with a cutter, sucks the trabecular meshwork (or the vitreous body), cuts it by the cutter, and feeds it to the control device together with the waste liquid.

A attaching type surgical instrument 300 (hereinafter, refer to as an instrument) shown in FIG. 18 is constructed by a leading end side cylinder portion 310 (attaching portion), a body side cylinder portion 320 (an attaching portion), and a connection portion 330 (an adjusting portion). A protection portion 311 is formed in the leading end side cylinder portion 310, and the leading end side cylinder portion 310, the body side cylinder portion 320 and the connection portion 330 are arranged in this order from a leading end side of the probe of the instrument 200. A through hole 312 to which the probe of the instrument 200 is inserted is formed in the leading end side cylinder portion 310, the body side cylinder portion 326 and the connection portion 330 at the center portion in an axial direction.

FIG. 18 is a partly cross sectional view in a state in which the instrument 300 is attached to the instrument 200, that is, the instrument 200 is inserted into the through hole 312. The instrument 300 is provided with a structure for attaching the instrument 200, and a structure for positioning the protection portion 311. A description will be given below of them.

A collar portion 312 and a fitting portion 313 are formed in the leading end side cylinder portion 310. The collar portion 312 is formed as a shape protruding outward in a peripheral direction on an outer peripheral surface of the leading end side cylinder portion 310. The fitting portion 313 is formed in such a manner that concave shapes and convex shapes heading for an axial direction are repeated along the peripheral direction, in a lower end of the drawing, that is, an end portion closer to the body in the leading end side cylinder portion 310.

A concave portion 332 and a thread groove portion 331 are formed in the connection portion 330. The concave portion 332 is a concave shape which is formed along the peripheral direction on an inner peripheral surface of the connection portion 330, and is fitted to the collar portion 312 of the leading end side cylinder portion 310. As a result, the leading end side cylinder portion 310 and the connection portion 330 are slidable in the peripheral direction. The thread groove portion 331 is a thread groove which is formed in a lower portion of the drawing than the concave portion 332 on the inner peripheral surface of the connection portion 330.

The body side cylinder portion 320 is provided with a thread groove portion 321, a fitting portion 323 and a bolt 322. The thread groove portion 321 is a thread groove which is formed on an outer peripheral surface of the body side cylinder portion 320, and is threadably engaged with the thread groove portion 331 of the connection portion 330. As a result, the connection portion 330 and the body side cylinder portion 320 relatively move in a vertical direction of the drawing by rotating the connection portion 330 around an axis.

The fitting portion 323 is formed in such a manner that concave shapes and convex shapes heading for an axial direction are repeated along the peripheral direction, in an upper end side of the drawing of the body side cylinder portion 320, and is fitted to the leading end side cylinder portion 310 and the fitting portion 313. As a result, the body side cylinder portion 320 and the leading end side cylinder portion 310 can relatively move in the vertical direction of the drawing while the fitting portions 313 and 323 are fitted.

The bolt 322 is threadably engaged with a through hole which is formed in a side surface of the body side cylinder portion 320. The body side cylinder portion 320 is fixed (positioned) in relation to the instrument 200 by fastening the bolt 322 in a state in which the instrument 200 is inserted into the instrument 300 so as to be set to an appropriate position. The body side cylinder portion 320 may be fixed by being pressed into with an appropriate pressure, without provision of the bolt 322.

Since the body side cylinder portion 320 is fixed, the connection portion 330 moves upward in the drawing while rotating, by rotating the connection portion 330 rightward around the axis in a state in which the body side cylinder portion 320 is fixed to the instrument 200 by the bolt 322. Since the collar portion 312 and the concave portion 332 are fitted, the leading end side cylinder portion 310 also moves upward in the drawing according to the upward movement of the connection portion 330. When the leading end side cylinder portion 310 moves upward, the rotation around the axis of the leading end side cylinder portion 310 is regulated (inhibited). Therefore, the leading end side cylinder portion 310 moves upward in the drawing in parallel without rotating. Of course, the leading end side cylinder portion 310 moves downward in the drawing in parallel by rotating the connection portion 330 in an inverse direction.

As mentioned above, the leading end side cylinder portion 310 moves in the vertical direction of the drawing in parallel, by inserting the probe of the instrument 200 into the instrument 300, fixing the body side cylinder portion 320 into the instrument 200 by the bolt 322, and rotating the connection portion 330 in this state. As a result, an appropriate positioning of the protection portion 311 can be achieved by adjusting an angle of rotation of the connection portion 330. In other words, it is possible to appropriately adjust a distance (d in FIG. 15) from (an upper end of) the protection portion 311 to the hole portion 221. Since the attaching type instrument 300 mentioned above can be used by being attached to the existing ophthalmic surgical instrument (for example, the vitreous body surgical instrument, the instrument for the glaucoma, however, the other ophthalmic surgical instruments may be employed without being limited to these instruments), it is possible to remarkably achieve a cost reduction effect.

The process for appropriately adjusting the distance from (the upper end of) the protection portion 311 to the hole portion 221 by rotating the connection portion 330 may be carried out by a manual step of the practitioner (the worker), however, since the process is a fine positioning, the process may be carried out by a machine. An example of a device for this purpose is shown in FIG. 19.

Figure 19:
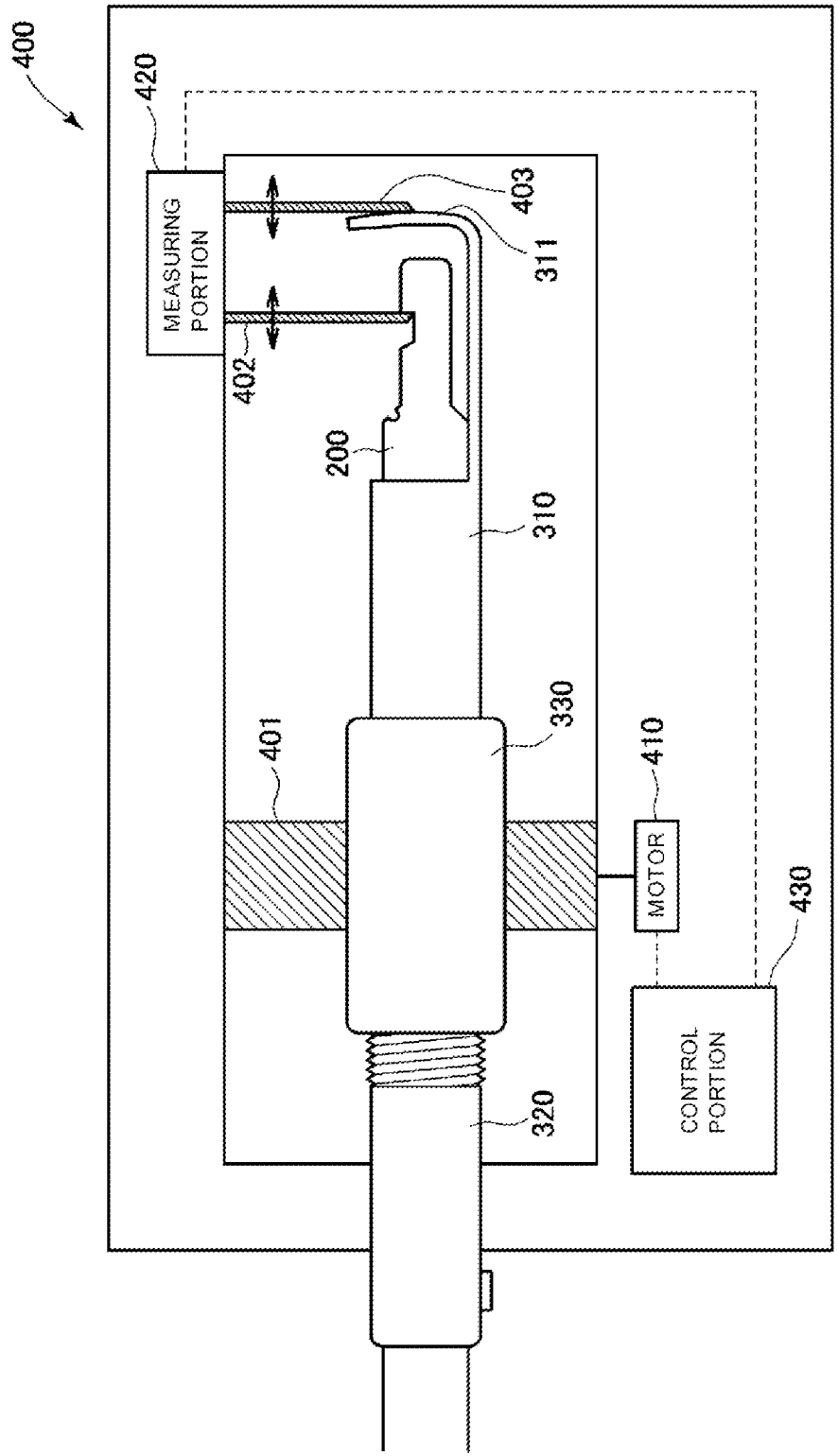
FIG. 19 is a view showing an example of a device for adjusting the attaching type surgical instrument.

A device 400 in FIG. 19 is a device for precisely positioning the protection portion 311 by arranging (grasping) the instrument 300 (which is fixed by the bolt 322 on the basis of the insertion of the instrument 200) within a casing. The device 400 is provided with a grasping portion 401, pinching portions 402 and 403, a motor 410, a measuring portion 420 and a control portion 430 as a main structure.

The grasping portion 401 is a region which grasps the connection portion 330 from an outer side in a diametrical direction. The grasping portion 401 may be arranged so as to be spaced in a peripheral direction or extend over a whole periphery. The pinching portions 402 and 403 form a rod-like region, are movable in a lateral direction of the drawing, and pinch the upper end (a right end of the drawing) of the protection portion 311 and the upper end (a right end of the drawing) of the hole portion 221 (with an appropriate pressure), as shown in FIG. 19.

The motor 410 is constructed, for example, by a step motor, and drives so that the grasping portion 401 rotates at a commanded angle around the axis. The measuring portion 420 measures a distance between respective leading ends of the pinching portions 402 and 403. A measuring method may employ a well-known electronic measuring method.

The control portion 430 is provided with the same structure as a typical computer, that is, a CPU for an information processing such as various calculations, a temporarily storing RAM serving as a processing area of the CPU, and a ROM storing necessary various information such as programs. The control portion 430 issues a command of an angle of rotation for setting the distance from (the upper end of) the protection portion 311 to an appropriate distance in the trabecular meshwork cutting operation to the motor 410, while monitoring results of measurement of the measuring portion 420.

The control by the control portion 430 may be set, for example, to a feedback control. In other words, a difference from a target value (a target distance) may be calculated by feeding back a measured value in the measuring portion 420, the results of calculation may be input to an appropriately designed controller, and the output may be set to an input value to the motor 410. According to the control mentioned above, it is possible to adjust the distance from (the upper end of) the protection portion 311 to the hole portion 221 to an optimum distance.

Figure 20:
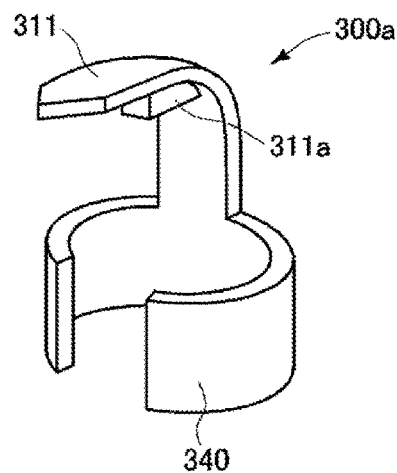
FIG. 20 is a perspective view of a second example of the attaching type surgical instrument.
Figure 21:
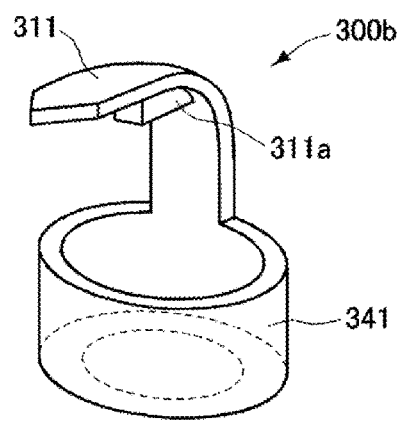
FIG. 21 is a perspective view of a third example of the attaching type surgical instrument.
Figure 22:
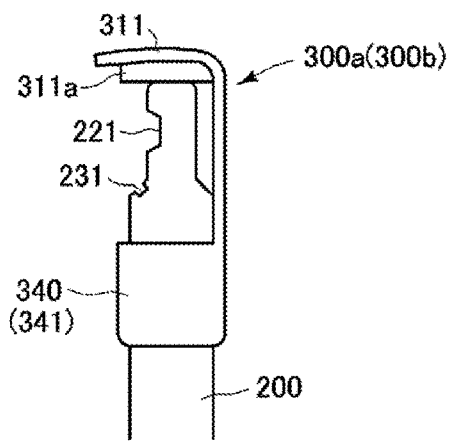
FIG. 22 is a view in the case that FIG. 20 or 21 is seen from a side direction.

The attaching type embodiment of the surgical instrument according to the present invention is not limited to the above example. The other embodiments are shown in FIGS. 20 to 21. FIG. 20 is a perspective view of a second example of the attaching type surgical instrument, FIG. 21 is a perspective view of a third example of the attaching type surgical instrument, and FIG. 22 is a view in the case that FIG. 20 or 21 is seen from a side direction. The examples in FIGS. 20 to 22 are the simpler embodiments than the example in FIG. 17, and are the embodiments which are attached only to the leading end of the existing instrument (for example, a description will be given of the case of the instrument 200).

An instrument 300a shown in FIG. 20 has a protection portion 311 above a curved portion 340 in the drawing, the curved portion 340 being extended to both right and left sides so as to be curved. The protection portion 311 may be formed as the same shape as the protection portion 21 mentioned above. The instrument 300a is installed, for example, from the leading end side of the instrument 200 so that the probe of the instrument 200 is inserted into the curved portion 340.

The fixing of the instrument 300a to the instrument 200 may be achieved, for example, by the probe of the instrument 200 being pressed into the curved portion 340. Alternatively, it is possible to employ an embodiment which fixes to the instrument 200 by inserting the probe of the instrument 200 into the curved portion 340 and thereafter caulking (pressing and deforming) the curved portion 340 from an outer side by an instrument such as a nipper. Alternatively, it is possible to form an adhesive agent (a pressure sensitive adhesive) layer in an inner side of the curved portion 340 and fix to the instrument 200 according to the adhesion (the pressure sensitive adhesion).

In an instrument 300b shown in FIG. 21, the protection portion 311 is formed above a cylinder portion 341 in the drawing, the cylinder portion having a cylindrical shape. The instrument 300b is installed, for example, from the leading end side of the instrument 200 so that the probe of the instrument 200 is inserted into the cylinder portion 341.

The fixing of the instrument 300b to the instrument 200 may be achieved, for example, by the probe of the instrument 200 being pressed into the cylinder portion 341. Alternatively, it is possible to employ an embodiment which fixes to the instrument 200 by inserting the probe of the instrument 200 into the cylinder portion 341 and thereafter caulking (pressing and deforming) the cylinder portion 341 from an outer side by an instrument such as a nipper. Alternatively, it is possible to form an adhesive agent (a pressure sensitive adhesive) layer in an inner side of the cylinder portion 341 and fix to the instrument 200 according to the adhesion (the pressure sensitive adhesion).

Even in the instruments 300a and 300b, it is necessary to make the distance d from the upper end of the protection portion 311 to the suction port 22 as shown in FIG. 15 appropriate as mentioned above. For this purpose, for example, a plate-shaped length adjusting portion 311a is formed in a lower side of the drawing of the protection portion 311, as shown in FIGS. 20 and 21.

On the basis of the formation of the length adjusting portion 311a, in the case that the instrument 300a or 300b is fixed to the instrument 200 so that the leading end of the instrument 200 comes into contact with the length adjusting portion 311a, as shown in FIG. 22, the distance d from the upper end of the protection portion 311 to the suction port 22 becomes a length which is suitable for cutting off the trabecular meshwork of the glaucoma operation in the meaning mentioned above. The thickness of the length adjusting portion 311a is set to be suited to the dimension of the existing instrument 200, in order to satisfy the requirement. It is possible to prepare the instrument for the glaucoma operation at a low cost by installing the instrument 300a or 300b according to the simple embodiment mentioned above to the existing instrument (which is not limited to the instrument 200).

What is claimed is:

1. A surgical instrument used in a cutting operation of a trabecular meshwork in the human eye, the surgical instrument comprising:
    a body portion utilizable as a handle or gripper, having a tubular shape;
    a rigid probe extending from one end of the body portion and having a tubular shape with a smaller diameter than the body portion;
    said probe comprising;
    an outflow port provided to dispense a cleaning liquid toward a trabecular meshwork,
    a suction port provided to collect the cleaning liquid dispensed from the outflow port and to suck the trabecular meshwork into the probe,
    a cutting blade to cut the trabecular meshwork sucked through the suction port,
    at least one passage being provided in the probe and the body portion to supply the cleaning liquid to the outflow port from a source outside the surgical instrument, and another passage being provided in the probe and the body portion to feed the sucked liquid and the cut trabecular meshwork from the suction port out of the surgical instrument,
    said surgical instrument further comprising a protector having a substantially L-shaped section extending along an outer profile of the probe and configured to protect an outer wall of a Schlemm's canal which is a part of a human eye that is not to be removed during the cutting of the trabecular meshwork, the protector being removably attached to an outer periphery or surface of the probe,
    said surgical instrument further comprising an attachment assembly comprising a first tubular portion at a leading or distal end and a second tubular portion at a trailing or proximal side, the protector being configured to extend from a leading or distal end of the first tubular portion, the second tubular portion being configured to fixedly attach to the probe, the first tubular portion and the second tubular portion being spaced a distance from one another, the attachment assembly further comprising an adjustment member connected on one side to the first tubular portion and on an opposite side to the second tubular portion and configured to adjust the distance between the first tubular portion and the second tubular portion and concomitantly adjust a distance between a distal end of the protector and a center of the suction port upon a coupling of the attachment assembly to the probe.

2. The surgical instrument according to claim 1, wherein the attachment assembly is configured to be attached to the outer periphery or surface of the probe.

3. The surgical instrument according to claim 2, wherein the protector is configured to extend from the first tubular portion along the outer profile of the probe, and a leading or distal end of the protector is configured so as to guide a leading or distal end of the probe along the outer wall of a Schlemm's canal.

4. The surgical instrument according to claim 3, wherein the first tubular portion is curved so as to surround the outer periphery or surface of the probe.

5. The surgical instrument according to claim 1, wherein the probe further comprises:
    an outer tubular member having a large diameter portion and a small diameter portion extending from a leading or distal end of the large diameter portion,
    an inner tubular member provided in the outer tubular member and extended in a proximal direction to the body portion the inner tubular member being translatable or rotatable in relation to the outer tubular member, and
    a driving member arranged in the body portion so as to drive the inner tubular member;
    said outflow port being provided in a side surface of the large diameter portion of the outer tubular member,
    said suction port being provided in a side surface of the small diameter portion of the probe,
    an opening being provided in a side surface of the inner tubular member at such a position so as to overlap the suction port to enable communication between the inside of the probe and an outer side of the probe,
    said cutting blade being provided at the opening of the inner tubular member to cut the trabecular meshwork sucked through the suction port owing to a relative translational motion or a relative rotating motion of the inner tubular member and the outer tubular member,
    an additional passage being provided in the body portion to supply power to drive the inner tubular member, the inner tubular member being operatively connectable via the additional passage to a power supply source provided outside of the surgical instrument,
    the at least one passage being provided in the probe and the body portion to supply the cleaning liquid to the outflow port, the at least one passage being connectable to a cleaning liquid supply source provided outside of the surgical instrument, and
    the another passage being provided in the probe and the body portion to feed the sucked liquid and the cut trabecular meshwork from the suction port, the another passage being connectable to a suction device provided outside of the surgical instrument.

6. The surgical instrument according to claim 1 wherein the adjustment member comprises a third tubular portion rotatably connected to the first tubular portion and the second tubular portion, the third tubular portion being screwingly connected to at least one of the first tubular portion and the second tubular portion.

7. A surgical instrument used in a cutting operation of a trabecular meshwork in the human eye, the surgical instrument comprising:
- a body portion utilizable as a handle or gripper, having a tubular shape;
- a rigid probe extending from one end of the body portion and having a tubular shape with a smaller diameter than the body portion;
- said probe comprising;
- an outflow port provided to dispense a cleaning liquid toward a trabecular meshwork,
- a suction port provided to collect the cleaning liquid dispensed from the outflow port and to suck the trabecular meshwork into the probe,
- a cutting blade to cut the trabecular meshwork sucked through the suction port,
- at least one passage being provided in the probe and the body portion to supply the cleaning liquid to the outflow port from a source outside the surgical instrument, and another passage being provided in the probe and the body portion to feed the sucked liquid and the cut trabecular meshwork from the suction port out of the surgical instrument, said surgical instrument further comprising a protector having a substantially L-shaped section extending along an outer profile of the probe and configured to protect an outer wall of a Schlemm's canal which is a part of a human eye that is not to be removed during the cutting of the trabecular meshwork, the protector being removably attached to an outer periphery or surface of the probe, wherein:
- the protector is formed as a part of an attachment which is configured to be attached to the outer periphery or surface of the probe;
- the attachment comprises at least one probe mounting portion to which the probe is attached, the protector is configured to extend from the at least one probe mounting portion along the outer profile of the probe, and the leading or distal end of the protector is configured so as to guide a leading or distal end of the probe along the outer wall of a Schlemm's canal;
- the at least one probe mounting portion is curved so as to surround the outer periphery or surface of the probe; and
- the attachment comprises a first tubular portion at a leading or distal end and a second tubular portion at a trailing or proximal side, said first and second tubular portions defining an attaching portion, the attachment further comprising a third tubular portion between the first tubular portion and the second tubular portion which surrounds or houses an adjusting member configured to adjust a distance between a leading or distal end of the protector and a center of the suction port upon a coupling of the attachment to the probe, the protector being configured to extend from a leading or distal end of the first tubular portion,
  - wherein a through hole into which the probe is inserted is provided in the attachment at a center location along an axial direction, and
  - wherein the first tubular portion is configured for movement in an axial direction while constrained from rotation around the axis, the second tubular portion is arranged to be fixed in relation to the probe, and the third tubular portion is arranged to be moved in the axial direction while being rotated around the axis, and
  - wherein the first tubular portion is configured for movement in the axial direction while constrained from rotation around the axis while the third tubular portion is being rotated,
  - whereby the distance between the leading or distal end of the protector and the center of the suction port is adjusted upon the rotation of the third tubular portion.

* * * * *